United States Patent
Komatsu et al.

(10) Patent No.: US 6,958,391 B2
(45) Date of Patent: Oct. 25, 2005

(54) METHOD FOR PURIFYING 5'-PROTECTED 2'-DEOXYPURINE NUCLEOSIDES

(75) Inventors: Hironori Komatsu, Mobara (JP); Toshiyuki Kouno, Mobara (JP); Katsutoshi Tsuchiya, Mobara (JP)

(73) Assignee: Mitsui Chemicals, Inc., Tokyo (JP)

( * ) Notice: Subject to any disclaimer, the term of this patent is extended or adjusted under 35 U.S.C. 154(b) by 51 days.

(21) Appl. No.: 10/120,500

(22) Filed: Apr. 12, 2002

(65) Prior Publication Data

US 2003/0009028 A1 Jan. 9, 2003

(30) Foreign Application Priority Data

Apr. 12, 2001 (JP) ........................................ 2001-113835

(51) Int. Cl.[7] ........................ C07H 21/00; C07H 21/02; C07H 21/04
(52) U.S. Cl. .................. 536/25.4; 536/25.3; 536/25.41; 536/28.6; 536/28.1
(58) Field of Search ............................. 536/25.3, 25.4, 536/25.41, 28.6, 28.1

(56) References Cited

U.S. PATENT DOCUMENTS 5,034,518 A * 7/1991 Montgomery et al. ..... 536/27.4

FOREIGN PATENT DOCUMENTS

| JP | 58-180500 A | 10/1983 |
| JP | 60-152495 A | 8/1985 |
| JP | 63-179889 A | 7/1988 |
| JP | 6-507883 A | 9/1994 |
| WO | WO 00/39138 A1 | 7/2000 |
| WO | WO 00/75154 A2 | 12/2000 |

* cited by examiner

*Primary Examiner*—Patrick Lewis
(74) *Attorney, Agent, or Firm*—Buchanan Ingersoll PC

(57) ABSTRACT

A method for efficiently purifying 5' protected 2'-deoxypurine nucleosides, efficient production of which has previously been difficult. Impurities can be separated by obtaining the 5' protected 2'-deoxypurine nucleoside as an inclusion crystal including a solvent such as that having a nitrile structure in order to purify the 5' protected 2'-deoxypurine nucleoside at a high purity. This invention enables synthesis of highly purified protected deoxypurine nucleosides easily on a large scale, which has previously been performed by column chromatography method.

8 Claims, No Drawings

METHOD FOR PURIFYING 5'-PROTECTED 2'-DEOXYPURINE NUCLEOSIDES

FIELD OF THE INVENTION

The present invention relates to a method of purifying 5'-protected 2'-deoxypurine nucleoside and a derivative thereof, as well as solvent-inclusion compounds thereof obtained by the method. More specifically, the present invention relates to a method of purifying 5'-protected 2'-deoxypurine nucleosides useful for producing them as well as a solvent inclusion compounds of 5'-protected 2'-deoxypurine nucleosides which are obtained by the purification method.

DESCRIPTION OF THE RELATED ART

5'-protected 2'-deoxy-β-purine nucleosides are compounds useful as raw materials for antisense DNA or the like, which has recently been developed.

In recent years, with developments in manufacturing genomic drugs, antisense DNA drugs or the like have rapidly been developed. Therewith, a DNA oligomer used as a raw material, and further, protected deoxy nucleosides used as raw materials for the oligomer are increasingly demanded. Regarding the pharmaceutical uses, it is necessary to use an extremely highly purified intermediate product to reduce generation of by-products based on impurities to a minimum.

As is clear from Japanese Patent Laid-Open Nos. 58-180500 and 63-179889, National Publication of International Patent Application No. 6-507883, etc., 5'-protected deoxypurine nucleosides have been purified by column chromatographic method till now. By this method, separation of impurities greatly different in their polarities or structures may be carried out relatively easily, but elimination of impurities having a similar structure is difficult. In particular, there are many cases where it is difficult to eliminate a 3'-substituted isomer that is a especially problematic impurity. In addition, since this method needs a large-scale purification device, in view of mass production and mass supply in the future, it cannot help saying that this method has a large problem.

Up till now, studies regarding elimination of impurities without using column chromatography have been made. Specifically, purification by reprecipitation method is disclosed in Japanese Patent Laid-Open No. 60-152495 and a PCT application, WO200075154. The reprecipitation method is a method in which, after a crude compound is dissolved in a soluble solvent, the compound is compulsively reprecipitated by addition of an insoluble solvent or dropping into an insoluble solvent. Consequently, its purification ability is basically low. Moreover, it is industrially difficult to appropriately control the amount ratio between the soluble solvent and the insoluble solvent. In addition, where the amount ratio of these solvents is set inappropriately, it easily results in oilification or generates a viscous precipitate so that purification is apt to end in failure. Actually, according to a method described in Japanese Patent Laid-Open No. 60-152495, in some cases, the purified product is obtained as a viscous syrupy substance, and, from an industrial viewpoint, this is a problem. Although some methods of forming an amorphous product by reprecipitation have been disclosed till now, no methods for obtaining a crystal by crystallization or recrystallization are known.

SUMMARY OF THE INVENTION

The present invention has been completed in view of the conventional problems, and the object of the present invention is to provide a purification method, which is efficient and does not need special facilities by which extremely highly purified 5'-protected 2'-deoxypurine nucleosides can be obtained.

As a result of intensive studies by the present inventors directed toward the above object, it has been found that, using a nitrile solvent such as acetonitrile, 5'-protected 2'-deoxypurine nucleosides can be obtained as a crystal that includes the solvent, and then it can be purified by a purification method using crystallization or recrystallization, thereby completing the present invention.

Thus, the present invention includes the following embodiments:

(1) A method of purifying a 5' protected 2'-deoxypurine nucleoside, which comprises the steps of:

obtaining a compound represented by the following formula (1):

wherein $R^1$ represents a 4-methoxytrityl group, 4,4'-dimethoxytrityl group or triphenylmethyl group, and B represents a purine group wherein an amino group is protected; in the form of inclusion crystals including a solvent, in a liquid medium comprising the solvent for inclusion; and recovering the inclusion crystals from the liquid medium.

(2) A method of purifying a 5' protected 2'-deoxypurine nucleoside according to the above section (1), wherein the solvent for inclusion is a nitrile compound substituted by a lower alkyl group or an aryl group.

(3) A method of purifying a 5' protected 2'-deoxypurine nucleoside according to the above section (2), wherein the solvent for inclusion is acetonitrile.

(4) A method of purifying a 5' protected 2'-deoxypurine nucleoside according to any one of the above sections (1) to (3), wherein a crude preparation comprising the compound of the formula (1) and a compound of the following formula (2);

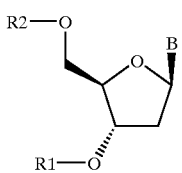

(2)

wherein R² represents a hydrogen atom, 4-methoxytrityl group, 4,4'-dimethoxytrityl group or triphenylmethyl group, and R¹ and B have the same definitions as stated above; is dissolved in the liquid medium and the compound of the formula (2) is removed into the liquid medium by recovering the compound of the formula (1) in the form of inclusion crystals from the liquid medium.

(5) A method of purifying a 5' protected 2'-deoxypurine nucleoside according to any one of the above sections (1) to (4), wherein the compound of the formula (1) is a compound of the following formula (3)

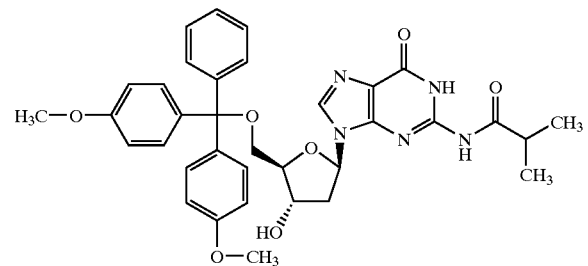

(3)

or a compound of the following formula (4)

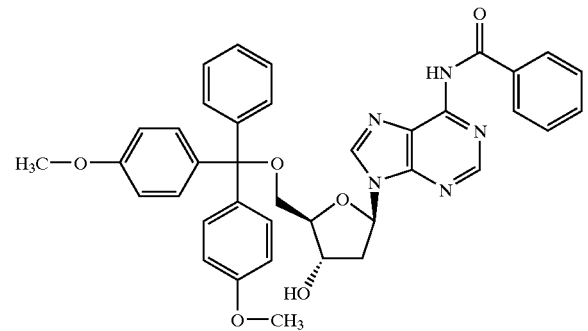

(4)

(6) A method of purifying a 5' protected 2'-deoxypurine nucleoside according to any one of the above sections (1) to (5), wherein the inclusion crystals of the compound of the formula (1) including the solvent for inclusion are recrystalized from a liquid medium consisting of the solvent for inclusion.

(7) A method of purifying a 5' protected 2'-deoxypurine nucleoside according to any one of the above sections (1) to (6), wherein the liquid medium consisting of a single solvent for inclusion.

(8) An inclusion compound represented by the following formula (5)

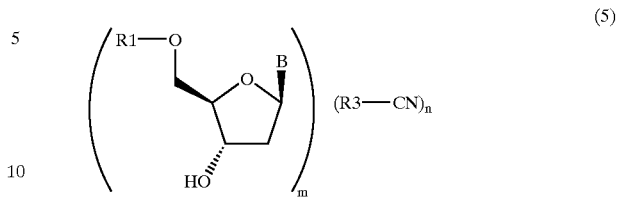

(5)

wherein R1 and B have the same definitions as stated above, m and n are independently an integer, R3 is a lower alkyl group or an aryl group.

DETAILED DESCRIPTION OF THE PREFERRED EMBODIMENTS

The present invention will be described in detail below.

The purine group forming the B in the formula (1) means a nucleic acid purine base of a natural or an unnatural nucleoside. Specific examples include adenine and guanine.

Examples of a protecting group for the amino group of the purine group include an alkyl group, an alkylacyl group and a benzoyl group.

The alkyl group may be straight chained or branched, or another functional group may be added thereto, as far as the function as the protecting group can be maintained. Examples of the alkyl group include a methyl group, an ethyl group, an n-propyl group, a 2-propyl group, an n-butyl group, an iso-butyl group, etc.

The alkylacyl group may be straight chained or branched, or may form a ring, or another functional group may be added thereto, as far as the function as the protecting group can be maintained. Examples of the alkylacyl group include an acetyl group, a propionyl group, an n-butyryl group, an iso-butyryl group, a pivaloyl group, an n-pentyloyl group, an iso-pentyloyl group, a cyclopropylcarbonyl group, a phenoxyacetyl group, etc.

The benzoyl group may not be substituted or may be substituted as far as the function as the protecting group can be maintained. One substituent may be at any one of positions 2, 3 and 4 of a phenyl group. Moreover, the substituent may be at a plurality of positions. Examples of the substituents include an alkyl group such as a methyl group, an ethyl group, a 2-propyl group, an n-butyl group or a tert-butyl group; a hydroxyl group; an alkyloxy group such as a methoxy group, an ethoxy group, an n-propyloxy group, a 2-propyloxy group or an n-butyloxy group; a nitro group; a halogen group such as a fluoro group, a chloro group, a bromo group or an iodo group; an amino group; an alkylamino group such as a methylamino group, an ethylamino group, an n-propylamino group, a dimethylamino group, a diethylamino group or a diisopropylamino group; an acyl group such as an acetyl group, a propionyl group or a benzoyl group; a phenyl group; a pyridinyl group, etc.

Specific examples of the benzoyl groups include a benzoyl group, a 2-chlorobenzoyl group, a 3-chlorobenzoyl group, a 4-chlorobenzoyl group, a 2-bromobenzoyl group, a 3-bromobenzoyl group, a 4-bromobenzoyl group, a 2-fluorobenzoyl group, a 3-fluorobenzoyl group, a 4-fluorobenzoyl group, a 2-methoxybenzoyl group, a 3-methoxybenzoyl group, a 4-methoxybenzoyl group, a 2-nitrobenzoyl group, a 3-nitrobenzoyl group, a 4-nitrobenzoyl group, a 2-aminobenzoyl group, a 3-aminobenzoyl group, a 4-aminobenzoyl group, a 2-methylaminobenzoyl group, a 3-methylaminobenzoyl group, a 4-methylaminobenzoyl group, a 2-dimethylaminobenzoyl group, a 3-dimethylaminobenzoyl group, a 4-dimethylaminobenzoyl group, a 4-phenylbenzoyl group, a 4-acetylbenzoyl group, etc.

Preferable Examples of a nitrile compound having a lower alkyl group or an aryl group, as the solvent for formation of the inclusion crystals, is those represented by the formula: R3-CN wherein R3 is a lower alkyl group or an aryl group. Examples of the alkyl group include a methyl group, an ethyl group, an n-propyl group, a 2-propyl group, an n-butyl group and an iso-butyl group. Examples of the aryl group include a phenyl group, a 4-methylphenyl group, a 4-methoxyphenyl group.

Examples of the nitrile compounds having the lower alkyl group or the aryl group include acetonitrile, propionitrile, n-butyronitrile, iso-butyronitrile, n-pentanenitrile, n-hexanenitrile, benzonitrile, etc. At least one of these nitrile compounds may be used.

Regarding m and n in the formula (5), m may be preferably an integer selected from 1 to 5, and n may be preferably an integer selected from 1 to 5.

The liquid medium for formation of the inclusion crystals may be composed either only of the solvent to be included in the crystals or of a mixture of the solvent for inclusion and other solvent(s) which does not form inclusion crystals at a ratio capable of mixing. Examples of the other solvents capable of being mixed with the solvent for inclusion include alcohols such as methanol, ethanol and isopropanol; esters such as ethyl acetate and butyl acetate; ketones such as acetone, methylethylketone and methylisobutylketone; ethers such as diethyl ether, diisopropyl ether, dioxane and tetrahydrofuran (THF); aromatic hydrocarbons such as benzene, toluene, cumene, xylene, mesitylene, diisopropylbenzene and triisopropylbenzene; halogenated hydrocarbons such as dichloromethane, chloroform and dichloroethane; pyridines such as pyridine, lutidine and quinoline; tertiary amines such as triethylamine and tributylamine; polar solvents such as dimethyl formamide (DMF), dimethyl imidazolidinone (DMI) and dimethyl sulfoxide (DMSO); water etc. At least one of these solvents may be used as the other solvent. The mixing ratio of the above listed other solvent(s) is 100% by weight or less with respect to the solvent for inclusion, preferably 20% by weight or less, and more preferably 10% by weight or less.

The term "inclusion crystal" including a solvent is herein used to mean that a solvent plays an auxiliary role to form a crystal structure, such that a crystal is formed in a form wherein a solvent is taken up into a crystal lattice thereof, or a complex is formed by a weak interaction between a crystal and a solvent. The inclusion form and the crystal structure are not particularly limited.

The amount of a nitrile solvent in crystallization and recrystallization are not particularly limited, as far as the amount is below the saturation solubility of a compound to be purified to the solution, but desirably the amount of the solvent is 5 times by weight or more to 150 times by weight or less of the amount of the compound of the formula (1), and further desirably it is 8 times by weight or more to 50 times by weight or less of the amount of the compound of the formula (1).

A temperature for crystallization and recrystallization are not particularly limited, but a temperature within a range from −10° C. to the boiling point of a solvent or a liquid medium is desired. Generally, purification can be performed more sufficiently by a single time of recrystallization, but purification at higher purity can also be realized by performing recrystallization repeatedly. A preferable liquid medium for recrystallization is that consisting of a solvent for inclusion alone and it is more preferable to use the same single solvent for inclusion in both of crystallization and recrystallization.

As stated above, according to the present invention, it becomes possible to efficiently purify protected 5' protected 2'-deoxypurine nucleosides.

EXAMPLES

The present invention will be further specifically described in the following examples. The examples are not intended to limit the scope of the invention.

Example 1

Production of a N2-isobutyryl-5'-O-(4,4'-dimethoxytrityl)-2'-deoxyguanosine and Acetonitrile (2:1) Complex 110 g (95% content) of N2-isobutyryl-2-deoxyguanosine was subjected to azeotropic dehydration with pyridine, and then dissolved in 2.4 L of pyridine. After adding 118.3 g of 4,4'-dimethoxytrityl chloride at room temperature, the mixture was stirred at room temperature for 3 hours. After neutralizing hydrochloric acid with sodium bicarbonate, the reaction solution was concentrated to about 400 g. After adding 1.5 L of ethyl acetate and 1.5 L of water were added thereto, the mixed solution was separated, and then washing with water was repeatedly performed until no N2-isobutyryl-2-deoxyguanosine as a raw material was found in an organic layer thereof. After washing with 1 kg of 20% sodium chloride solution, drying with sodium sulfate was performed. After performing filtration, a solvent was removed and ethyl acetate was then added so that the total amount became 700 g.

This solution was dropped into 3,200 g of diisopropyl ether, while intensively stirring, and thereafter the obtained solution was stirred at room temperature for 2 hours. The solid obtained by filtration was subjected to vacuum drying at 50° C., and after confirming that a constant weight was obtained, it was dissolved in 4.4 L of acetonitrile at room temperature. After stirring at room temperature for 4 hours, the deposited solid was filtrated. The obtained product was subjected to vacuum drying at room temperature for 4 hours and then an NMR analysis. It was found by the analysis that the obtained product included 2 molecules of acetonitrile per one molecule of the target compound to be purified. Where vacuum drying was performed at 40° C. for 12 hours, it was found by the subsequent NMR analysis that the obtained product included one molecule of acetonitrile per one molecule of the target compound to be purified.

Where vacuum drying was performed at 50° C. for 15 hours, it was found by the subsequent NMR analysis that the obtained product included 0.67 molecule of acetonitrile per one molecule of the target compound to be purified. Further, where vacuum drying was performed at 55° C. until a constant weight was obtained (for 24 hours), it was found by the subsequent NMR analysis that the obtained product included 0.5 molecule of acetonitrile per one molecule of the target compound to be purified. By X-ray diffraction (XRD), it was found that the obtained product was a crystal in any of the above dry conditions. Moreover, by TG-DTA analysis, it was found that, regarding a crystal included 0.5 molecule of acetonitrile per one molecule of the target compound to be purified, that was obtained by drying until a constant weight was obtained, the weight of the crystal was not reduced until a temperature was raised to the temperature for endothermic reaction (81° C. to 93° C.), the crystal having no attached solvent. The yield was 168 g (yield rate 84.8%). As a result of an analysis by HPLC (UV254 nm), the purity was 99.7% by area. The largest impurity was N2-isobutyryl-3',5'-O-bis(4,4'-dimethoxytrityl)-2'-deoxyguanosine (0.17% by area).

NMR (DMSO-$d_6$) δ:12.1 (s, 1H), 11.7 (s, 1H), 8.1 (s, 1H), 7.3 (m, 2H), 7.3–7.3 (m, 7H), 6.9–6.8 (m, 4H), 6.3 (t, J=6 Hz, 1H), 5.4 (m, 1H), 4.4 (m, 1H), 3.97 (m, 1H), 3.724 (s, 3H), 3.719 (s, 3H), 3.2 (m, 1H), 3.1 (m, 1H), 2.8 (m, 1H), 2.4 (m, 1H), 2.1 (s, 3/2H, acetonitrile), 1.1 (d, J=6.8 Hz, 6H).

$^1$R(KBr) cm$^{-1}$: 3398, 3238, 2935, 2838, 1679, 1609, 1561, 1509, 1252, 1178, 1034, 830 (Absorption of acetonitrile derived from nitrile was weak and was not observed.)

Example 2

Production of N6-benzoyl-5'-O-(4,4'-dimethoxytrityl)-2'-deoxyadenosine 45.0 g (0.127 mol) of N6-benzoyldeoxyadenosine was dissolved in 500 ml of pyridine followed by azeotropic dehydration, and then the obtained product was dissolved in 500 ml of pyridine. While stirring, 42.9 g (0.127 mol) of 4,4'-dimethoxytrityl chloride was added thereto, and the mixture was further stirred at room temperature for 2.5 hours. After 12.8 g of sodium bicarbonate was added thereto and the mixture was stirred at room temperature for 30 minutes, a solvent was removed at reduced pressure. To the residue, 830 ml of methylisobutylketone was added, and while stirring 830 ml of water was further added thereto followed by stirring for 10 minutes. Subsequently, an organic layer thereof was collected, washed with a saturated saline solution and dried with sodium sulfate, and thereafter a solvent was removed at reduced pressure. The residue was dropped in 800 ml of diisopropyl ether that was intensively stirred, and the generated precipitate was collected by filtration.

The precipitate was recrystallized from 750 ml of acetonitrile, and the crystal product was collected by filtration. As a result of an NMR analysis, the product included one molecule of acetonitrile per one molecule of the target compound to be purified. When the crystal product was subjected to vacuum drying, acetonitrile was lost. The weight was 66.7 g. When the obtained product was analyzed by high performance liquid chromatography [ODS: octadecyl silica gel column, acetonitrile/water (8:2)], using a UV detector (254 nm), the purity was 99.5%. The yield of N6-benzoyl-5'-O-(4,4'-dimethoxytrityl)-2'-deoxyadenosine was 79.4%. The largest impurity was N6-benzoyl-3',5'-O-bis(4,4'-dimethoxytrityl)-2'-deoxyadenosine (0.15% by area).

Reference Example 1

Production of N2-isobutyryl-3',5'-O-bis(4,4'-dimethoxytrityl)-2'-deoxyguanosine

After the filtrate obtained by the recrystallization in Example 1 was concentrated, the concentrate residue was purified by column chromatography (ethyl acetate/hexane). The purified fraction was concentrated to obtained a yellow oily product. The yellow oily product was then dropped into diisopropyl ether and the precipitate thus formed was recovered by filtration and dried, whereby the titled compound was obtained as a light yellow powder.

$^1$H NMR(400 MHz, DMSO-$d_6$) δ 12.1(1H,s), 11.5(1H,s), 7.9(1H,s), 7.5–7.2(18H,m), 6.8(8H,m), 6.2(1H,m), 4.4(1H, m), 3.8(1H,m), 3.7(12H,s), 3.6(1H,m), 3.0(1H,m), 2.8(1H, m), 2.4(1H,m), 1.8(1H,m), 1.1(6H,m), 1.0(6H,m).

Reference Example 2

Production of N2-isobutyryl-5'-O-(tert-butyldimethylsilyl)-2'-deoxyguanosine

N2-isobutyryl-2'-deoxyguanosine (20.5 g) was dissolved in 200 ml of DMF. After 18.5 g of imidazole was dissolved in the resultant solution by addition, 21.4 g of tert-butyldimethylsilyl chloride was then added. DMF (100 ml) was further added and the solution was stirred at room temperature. After 8 hours, extraction using chloroform was carried out and the organic layer was washed by a saturated aqueous solution of sodium chloride and dried with anhydrous magnesium sulfate. After concentration of the extract, the target compound was separated by column chromatography (methanol/chloroform). The fraction solution including the target compound was prepared and concentrated to obtain 20.5 g of the titled compound (yield; 74%).

$^1$ H NMR(400 MHz, CDCl$_3$) δ:12.4(1H,s), 10.9(1H,s), 8.0(1H,s), 6.0(1H,dd,J=6.4,6.4 Hz), 4.6(2H,m), 4.1(1H,d,J= 2.0 Hz), 3.8(2H,m), 2.9(1H,m), 2.4(2H,m), 1.3(6H,m), 0.8 (9H,s), 0.2(6H,s).

Reference Example 3

Production of N2-isobutyryl-5'-O-(tert-butyldimethylsilyl)-3'-O-(4,4'-dimethoxytrityl)-2'-deoxyguanosine N2-isobutyryl-5'-O-(tert-butyldimethylsilyl)-2'-deoxyguanosine (19.8 g) was dissolved in 100 ml of anhydrous pyridine. 4,4'-dimethoxytrityl chloride (1.66 g) was added to the resultant solution and 140 ml of anhydrous pyridine was further added, follow by stirring at 40° C. After the reaction completed, the reaction mixture was neutralized by sodium hydrogen carbonate and pyridine was distilled off. Extraction using chloroform was carried out and the extract was washed by a saturated aqueous solution of sodium chloride and dried with anhydrous magnesium sulfate. The extract was concentrated and purified by column chromatography (ethyl acetate/hexane) to obtain 25.8 g of the titled compound (yield: 78%).

$^1$H NMR(400 MHz, CDCl$_3$) δ: 11.9(1H,s), 8.1(1H,s), 7.8(1H,s), 7.5–7.2(9H,m), 6.8(4H,m), 6.2(1H,dd,J=6.0,8.4 Hz), 4.4(1H,m), 4.1(1H,m), 3.8(6H,s), 3.6(1H,dd,J=8.8,11.2 Hz), 3.3(1H,dd,J=2.8,11.2 Hz), 2.6(1H,m), 2.0–1.6(2H,m), 1.3(6H,m), 0.8(9H,s), 0.02(6H,s).

Reference Example 4

Production of N2-isobutyryl-3'-O-(4,4'-dimethoxytrityl)-2'-deoxyguanosine

N2-isobutyryl-5'-O-(tert-butyldimethylsilyl)-3'-O-(4,4'-dimethoxytrityl)-2'-deoxyguanosine (25 g) was dissolved in 200 ml of dry THF. A THF solution (40 ml) of tetrabutylammonium fluoride was added to the resultant solution and 100 ml of dry THF was further added, followed by stirring at room temperature. After 8 hours, extraction using chloroform was carried out, and the extract was washed by a saturated solution of sodium chloride and dried with anhydrous magnesium sulfate. The extract was then concentrated and purified by column chromatography (ethyl acetate/hexane/methanol) to obtain 12.9 g of the titled compound as a white powder (yield: 60%).

$^1$H NMR(400 MHz, CDCl$_3$)δ 12.0(1H,s), 8.3(1H,s), 7.7(1H,s), 7.5–7.2(9H,m), 6.8(4H,m), 6.2(1H,dd,J=5.2, 10 Hz), 4.5(1H,m), 4.0(1H,m), 3.8(6H,s), 3.7(1H,m), 3.3(1H,m), 2.6(1H,m), 2.4(1H,m), 1.7(1H,m), 1.2(6H,m).

Comparative Example 1

In respect of an ability to eliminate impurities such as the 3'-substituted isomer [N2-isobutyryl-3'-O-(4,4'-dimethoxytrityl)-2'-deoxyguanosine] or the 3',5'-multiple substituted form [N2-isobutyryl-3',5'-O-bis(4,4'-dimethoxytrityl)-2'-deoxyguanosine], there was made a comparison between a method involving recrystallization with an acetonitrile solvent and a purification method involving reprecipitation using dichloromethane as a soluble solvent, and hexane or toluene as an insoluble solvent. In addition, the yield rate of a product of interest, [N2-isobutyryl-5'-O-(4,4'-dimethoxytrityl)-2'-deoxyguanosine], was compared between both methods, and also thermal analysis (DSC: endothermic peak, endothermic energy) of the obtained crystal was carried out. The results thus obtained are shown in Table 1, which include the contents of the 3 isomer and the multi-substituted compound in the crude crystal preparation, and the crystals after recrystalization using each solvent.

TABLE 1

| | Purification solvent | | | |
|---|---|---|---|---|
| | Rough crystal | Acetonitrile | Dichloromethane/ hexane | Dichloromethane/ toluene |
| 3'-isomer | 4.9% | 0.08% | 3.06% | 0.76% |
| Multiple substituted form | 2.76% | 0% | 2.27% | 0.36% |
| Yield rate | | 95% | 83% | 76% |

TABLE 1-continued

| | Purification solvent | | | |
|---|---|---|---|---|
| | Rough crystal | Acetonitrile | Dichloromethane/ hexane | Dichloromethane/ toluene |
| Endothermic peak | | 81° C. | No clear endothermic peaks were shown. | |
| Endothermic energy | | 28 J/g | | |

(% is based on weight.)

As is clear from the results concerning DSC, it was revealed that, since the endothermic peaks of the compounds were different, the crystal types of the compounds were also different. Regarding the large endothermic energy, it was further revealed that the product obtained from acetonitrile alone was formed as crystals.

Reference Example 5

Production of N6-benzoyl-3',5'-O-bis(4,4'-dimethoxytrityl)-2'-deoxyadenosine

After the filtrate obtained by the recrystallization in Example 2 was concentrated, the concentrate residue was purified by column chromatography (ethyl acetate/hexane). The purified fraction was concentrated to obtained a yellow oily product. The yellow oily product was then dropped into diisopropyl ether and the precipitate thus formed was recovered by filtration and dried, whereby the titled compound was obtained as a light yellow powder.

$^1$H NMR(400 MHz, DMSO-d6) δ: 11.2(1H,br), 8.6(1H, s), 8.5(1H,s), 8.0(2H,m), 7.7–6.7(29H,m), 6.4(1H,m), 4.3 (1H,m), 4.1(1H,m), 3.8(14H,s), 3.6(1H,m), 3.0(1H,m), 1.0 (6H,m).

Reference Example 6

Production of N6-benzoyl-5'-O-(tert-butyldimethylsilyl)-2'-deoxyadenosine

N6-benzoyl-2'-deoxyadenosine (20.95 g ) was dissolved in 200 ml of DMF. Imidazole (15.7 g) was dissolved to the resultant solution by addition. Then, 20.8 g of tert-butyldimethylsilyl chloride was added. DMF (100 ml) was further added and the solution was stirred at room temperature. After 8 hours, extraction using chloroform was carried out and the organic layer was washed by a saturated aqueous solution of sodium chloride and dried with anhydrous magnesium sulfate. After concentration of the extract, the target compound was purified by column chromatography (methanol/chloroform) to obtain 16.1 g of the titled compound (yield; 61%).

$^1$H NMR(400 MHz, CDCl$_3$) δ:9.1(1H,s), 8.8(1H,s), 8.3 (1H,s), 8.0(2H,d,J=12.4 Hz), 7.6–7.5(3H,m), 6.6(1H,dd,J= 6.8,6.8Hz), 4.7(1H,m), 4.1(1H,m), 3.9(2H,m), 2.8(1H,m), 2.6(1H,m), 0.9(9H,s), 0.1(6H,s).

Reference Example 7

Production of N6-benzoyl-5'-O-(tert-butyldimethylsilyl)-3'-O-(4,4'-dimethoxytrityl)-2'-deoxyadenosine N6-bezoyl-5'-O-(tert-butyldimethylsilyl)-2'-deoxyadenosine (16.1 g) was dissolved in 100 ml of anhydrous pyridine. 4,4'-dimethoxytrityl chloride (12.8 g) and anhydrous pyridine (140 ml) were further added, follow by stirring at 45° C. After the reaction completed, the reaction mixture was neutralized by sodium hydrogen carbonate, and pyridine was distilled off. Extraction using chloroform was carried out and the extract was washed by a saturated aqueous solution of sodium chloride and dried with anhydrous magnesium sulfate. The extract was concentrated and then purified by column chromatography (ethyl acetate/hexane) to obtain 16.7 g of the titled compound (yield: 63%).

$^1$H NMR(400 MHz, CDCl$_3$) δ: 9.1(1H,s), 8.9(1H,s), 8.3 (1H,s), 8.1(2H,d,J=7.2 Hz), 7.7–7.3(12H,m), 6.9(4H,m), 6.7 (1H,dd,J=5.6,8.4 Hz), 4.5(1H,m), 4.2(2H,m), 3.9(6H,s), 3.7 (1H,dd,J=2.4,11.2 Hz), 3.4(1H,dd,J=8.4,11.2 Hz), 2.2–2.1 (2H,m), 2.0–1.6(2H,m), 1.3(1.5H,m), 0.9(9H,s), 0.03(6H,s).

Reference Example 8

Production of N6-bezoyl-3'-O-(4,4'-dimethoxytrityl)-2'-deoxyadenosine

N6-benzoyl-5'-O-(tert-butyldimethylsilyl)-3'-O-(4,4'-dimethoxytrityl)-2'-deoxyadenosine (16.2 g) was dissolved in 200 ml of dry THF. A THF solution (31 ml) of tetrabutylammonium fluoride was added to the resultant solution and 100 ml of dry THF was further added, followed by stirring at room temperature. After 8 hours, THF was distilled off and extraction using chloroform was carried out. The extract was then washed by a saturated solution of sodium chloride and dried with anhydrous magnesium sulfate. The extract was then concentrated and purified by column chromatography (ethyl acetate/hexane/methanol) to obtain 13.8 g of the titled compound as a white powder (yield: 98%).

$^1$H NMR(400 MHz, CDCl$_3$) δ:9.0(1H,br), 8.7(1H,s), 8.1 (1H,s), 8.0(2H,m), 7.7–7.2(12H,m), 6.9(4H,m), 6.4(1H,m), 4.6(1H,m), 4.1(1.3H,m), 3.8(6H,s), 3.7(1H,m), 3.3(1H,m), 2.7(1H,m), 2.0(2H,m), 2.0–1.6(2H,m), 1.7(1H,m), 1.3(2H, m).

Comparative Example 2

In respect of an ability to eliminate impurities such as the 3'-substituted isomer (N6-benzoyl-3'-O-(4,4'-dimethoxytrityl)-2'-deoxyadenosine or the 3',5'-multiple substituted form [N6-benzoyl-3',5'-O-bis(4,4'-dimethoxytrityl]-2'-deoxyadenosine), there was made a comparison between a method involving recrystallization with an acetonitrile solvent and a purification method involving reprecipitation with dichloromethane as a soluble solvent and a mixed solution of t-butylmethyl ether and hexane (1:2) as an insoluble solvent. In addition, the yield rate of a product of interest, [N6-benzoyl-5'-O-(4,4'-dimethoxytrityl)-2'-deoxyadenosine], was compared between both methods, and also thermal analysis (DSC: endothermic peak, endothermic energy) of the obtained crystal was carried out.

The results thus obtained are shown in Table 2, which include the contents of the 3' isomer and the multi-substituted compound in the crude crystal preparation, and the crystals after recrystallization using each solvent.

TABLE 2

| | Rough crystal | Purification solvent | |
| --- | --- | --- | --- |
| | | Acetonitrile | Dichloromethane/ t-butylmethyl ether-hexane (1:2) |
| 3'-isomer | 1.84% | 0.06% | 2.24% |
| Multiple substituted form | 4.03% | 0% | 1.43% |
| Yield rate | | 87% | 96% |
| Endothermic Peak | | 114° C. | 125° C. |
| Endothermic energy | | 34 J/g | |

(% is based on weight.)

As is clear from the results concerning DSC, it was revealed that, since the endothermic peaks of the compounds were different, the crystal types of the compounds were also different. Regarding the large endothermic energy, it was further revealed that the product obtained from acetonitrile alone was formed as crystals.

The condition of HPLC for each compound is as follows:
(1) HPLC conditions in Comparative Examples 1 and 2 (analysis of the amount of the multiple substituted form):
Column: Develosil TMS-UG-5
150 mm×φ4.6
Flow rate: 1.0 mL/min
Column temperature: 40° C.
Detection wavelength: 254 nm
Mobile phase: gradient conditions

| Time (min) | Liquid B (%) |
| --- | --- |
| 0 | 20 |
| 15 | 70 |
| 35 | 100 |
| 40 | 100 |
| 45 | 20 |
| 60 | STOP |

[Liquid A]
100 mL of 100 mM triethylamine-acetic acid (pH7)/880 mL of water/20 mL of acetonitrile
[Liquid B]
100 mL of 100 mM triethylamine-acetic acid (pH7)/900 mL of acetonitrile
(2) HPLC conditions in Comparative Examples 1 and 2 (analysis of the amount of the 3'-isomer):
Column: Develosil TMS-UG-5
150 mm×φ4.6
Mobile phase: acetonitrile-water (55:45)
Flow rate: 1.0 mL/min
Column temperature: 40° C.
Detection wavelength: 254 nm
Conditions for thermal analysis:
   Apparatus: DSC-7 (PerkinElmer)
   Rate of temperature rise: 10° C./min
Condition for XRD:
   Apparatus: RAD-RVC (RIGAKU)
   X-ray target: Cu 50 kV 200 mA.
According to the present invention, a method capable of mass production enables production of highly purified protected 2'-deoxypurine nucleosides more efficiently than conventional methods.

What is claimed is:

1. A method of purifying a 5' protected 2'-deoxypurine nucleoside, which comprises the steps of:

(a) preparing a solution of a compound represented by the following formula (1):

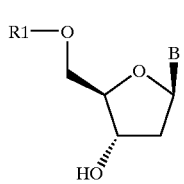

(1)

wherein $R^1$ represents a 4-methoxytrityl group, 4,4'-dimethoxytrityl group or triphenylmethyl group, and B represents a purine group wherein an amino group is protected; in a liquid medium comprising a solvent for forming inclusion crystals comprising said solvent and the compound of formula (1);

(b) forming inclusion crystals comprising said solvent and the compound of formula (1) in said solution by treating said solution alone; and (c) recovering said inclusion crystals from the liquid medium of the solution.

2. A method of purifying a 5' protected 2'-deoxypurine nucleoside according to claim 1, wherein the solvent for inclusion is a nitrile compound substituted by a lower alkyl group or an aryl group.

3. A method of purifying a 5' protected 2'-deoxypurine nucleoside according to claim 2, wherein the solvent for inclusion is acetonitrile.

4. A method of purifying a 5' protected 2'-deoxypurine nucleoside according to claim 1, wherein a crude preparation comprising the compound of the formula (1) and a compound of the following formula (2):

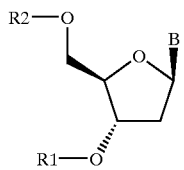

(2)

wherein $R^2$ represents a hydrogen atom, 4-methoxytrityl group, 4,4'-dimethoxytrityl group or triphenylmethyl group, have the same definitions as stated above; is dissolved in the liquid medium and the compound of the formula (2) is removed into the liquid medium by recovering the compound of the formula (1) in the form of inclusion crystals from the liquid medium.

5. A method of purifying a 5' protected 2'-deoxypurine nucleoside according to claim 1, wherein the compound of the formula (1) is a compound of the following formula (3)

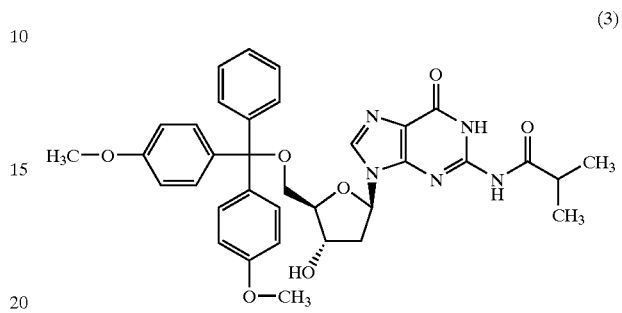

(3)

or a compound of the following formula (4)

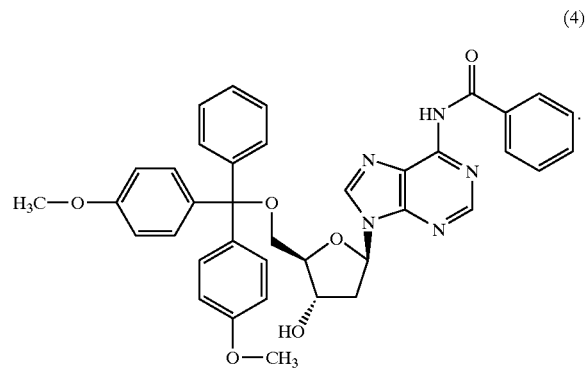

(4)

6. A method of purifying a 5' protected 2'-deoxypurine nucleoside according to claim 1, wherein the inclusion crystals of the compound of the formula (1) including the solvent for inclusion are recrystallized from a liquid medium consisting of the solvent for inclusion.

7. A method of purifying a 5' protected 2'-deoxypurine nucleoside according to claim 1, wherein the liquid medium consists of a single solvent for inclusion.

8. A method of purifying a 5' protected 2'-deoxypurine nucleoside according to claim 6, wherein the liquid medium consists of a single solvent for inclusion.

* * * * *